United States Patent
Wen

(10) Patent No.: US 6,673,137 B1
(45) Date of Patent: Jan. 6, 2004

(54) APPARATUS AND METHOD FOR PURIFYING AIR IN A VENTILATION SYSTEM

(76) Inventor: Sheree H. Wen, 796 Longhill Rd. West, Briarcliff Manor, NY (US) 10510

( * ) Notice: Subject to any disclaimer, the term of this patent is extended or adjusted under 35 U.S.C. 154(b) by 0 days.

(21) Appl. No.: 09/996,861

(22) Filed: Nov. 27, 2001

(51) Int. Cl.$^7$ ................................................ B01D 50/00
(52) U.S. Cl. .......................... 96/224; 96/227; 422/121; 422/124
(58) Field of Search .......................... 96/223, 224, 226, 96/227; 422/121, 124; 261/DIG. 42

(56) References Cited

U.S. PATENT DOCUMENTS

| | | |
|---|---|---|
| 1,891,256 A | 12/1932 | Blide |
| 3,230,033 A * | 1/1966 | Hamilton et al. ............ 422/121 |
| 3,478,758 A | 11/1969 | Davies |
| 3,817,703 A | 9/1971 | Atwood |
| 3,915,180 A | 10/1975 | Jacobs |
| 3,926,556 A * | 12/1975 | Boucher ....................... 422/21 |
| 4,207,286 A | 6/1980 | Gut Boucher |
| 4,468,372 A | 8/1984 | Seifert et al. |
| 4,513,470 A | 4/1985 | Toya |
| 4,536,914 A | 8/1985 | Levine |
| 4,542,557 A | 9/1985 | Levine |
| 4,577,365 A | 3/1986 | Yuen |
| 4,591,485 A | 5/1986 | Olsen et al. |
| 4,610,048 A | 9/1986 | Ishihara et al. |
| 4,836,684 A | 6/1989 | Javorik et al. |
| 4,924,548 A | 5/1990 | Touya et al. |
| 5,120,499 A | 6/1992 | Baron |
| 5,244,629 A | 9/1993 | Caputo et al. |
| 5,320,805 A | 6/1994 | Kramer et al. |
| 5,364,645 A | 11/1994 | Lagunas-Solar |
| 5,492,882 A | 2/1996 | Doughty et al. |
| 5,589,396 A | 12/1996 | Frye et al. |
| 5,593,476 A | 1/1997 | Coppom |
| 5,647,890 A | 7/1997 | Yamamoto |
| 5,651,811 A | 7/1997 | Frey et al. |
| 5,656,063 A | 8/1997 | Hsu |
| 5,725,623 A | 3/1998 | Bowerman et al. |
| 5,779,769 A | 7/1998 | Jiang |
| 5,927,304 A | 7/1999 | Wen |
| 5,944,873 A | 8/1999 | Jager et al. |
| 6,029,712 A | 2/2000 | Dougherty |
| 6,056,808 A | 5/2000 | Krause |
| 6,063,170 A * | 5/2000 | Deibert ........................ 96/224 |
| 6,094,775 A | 8/2000 | Behmer |
| 6,171,375 B1 | 1/2001 | Howie |
| 6,190,437 B1 | 2/2001 | Forsyth |
| 6,203,600 B1 | 3/2001 | Loreth |
| 6,295,692 B1 | 10/2001 | Shideler |
| 6,296,692 B1 | 10/2001 | Gutmann |
| 6,333,004 B1 | 12/2001 | Sheldon |
| 6,434,785 B1 | 8/2002 | Vandenbelt et al. |
| 6,468,433 B1 | 10/2002 | Tribelski |
| 2001/0043887 A1 | 11/2001 | Morneault |

FOREIGN PATENT DOCUMENTS

| | | |
|---|---|---|
| DE | 3739979 A1 | 6/1989 |
| FR | 2599255 | 12/1987 |
| GB | 947699 | 9/1961 |
| GB | 2162424 | 2/1986 |
| JP | 62-282686 | 12/1987 |
| JP | 2-43984 | 2/1990 |

* cited by examiner

*Primary Examiner*—Robert A. Hopkins
(74) *Attorney, Agent, or Firm*—Robert D. Katz; Cooper & Dunham

(57) ABSTRACT

An air purifier includes a housing having a purification chamber with an inlet to the housing for drawing in contaminated air and an outlet from the housing for releasing purified air. The air purifier also includes an inlet for introducing a fluid containing a source of antimicrobial ions into the purification chamber. The air purifier also includes at least one microwave radiation source and at least one ultraviolet radiation source which work in combination to increase the effectiveness of the antimicrobial ions. Also included are filters for removing airborne particulates and adsorbing antimicrobial ions from treated air.

9 Claims, 3 Drawing Sheets

APPARATUS AND METHOD FOR PURIFYING AIR IN A VENTILATION SYSTEM

FIELD OF THE INVENTION

This invention relates to an apparatus for purifying air flowing through a heating, air conditioning or other ventilation system, and more particularly to an apparatus which uses high energy microwave and ultraviolet radiation, along with an antimicrobial fluid to kill contaminants such as bacteria and viruses dispersed in the air flowing through the ventilation system. The invention further relates to a self-contained air purification module.

BACKGROUND OF THE INVENTION

Various methods of removing bacteria viruses and other contaminants exist for use as stand alone system or as a module installed in a new or existing ventilation system. Various types of filters remove contaminants above certain size by physically separating particles over a certain size, which may include dust particles, bacteria and viruses. Other systems use energy in the form of light or radiation to kill undesirable bacterial and viral micro-organisms. Still other filtration systems use activated charcoal or a similar material to adsorb unwanted odors, airborne particles, cigarette smoke, and pollutants from the air in an enclosed space.

Many persons have attempted to improve air cleaners for ventilation systems. For example, U.S. Pat. No. 6,203,600 (Loreth) discusses a device for air cleaning. The device includes a precipitator for use in an air purification device, especially one removing electrically charged particles. U.S. Pat. No. 6,296,692 (Gutmann) discusses free standing air purifier enclosed in a housing, for use in cleaning the air in a room. The device uses an electrostatic air cleaning unit, operating at lower voltages, which ionizes debris contained in the air while eliminating ozone formation.

U.S. Pat. No. 5,779,769 (Jiang) illustrates a lamp including an indoor air purifier. The lamp draws air into its interior, through a purification system including activated charcoal and an electrostatic air cleaner, and expels it back into the room.

In U.S. Pat. No. 6,056,808 (Krause), an apparatus ionizes air to remove particulate matter. According to the patentee, high voltage electrodes ionize airborne particulates, and an ionic wind is created between the electrode and the duct. The use of high horsepower blowers enables use of the device in office buildings.

Similarly, U.S. Pat. No. 5,656,063 (Hsu) discloses an air cleaner with separate ozone gas and ionized air outputs. Air is drawn through a multi-layered filter, then through an ionizer to induce a negative electric charge. The negative ions precipitate when passing through a filter having a positive charge. An ozone generator mixes with the air to provide further cleansing.

Likewise, U.S. Pat. No. 5,647,890 (Yamamoto) discloses a clog resistant filter to remove fine particulates and an induced voltage electrode to capture contaminant particles in a filter material.

U.S. Pat. No. 5,593,476 (Coppom) also discusses an air filtration apparatus. The device has a fibrous filter positioned between two electrodes, and corona pre-charger positioned upstream of the electrodes and filter.

Finally, U.S. application Ser. No. 2001043887 (Moreault), discusses a device which includes a high mass-flow rate air-mover and a low mass-flow rate ultraviolet decontamination device.

The threat of airborne hazards has created a need for an efficient air purifying system. It is therefore an object of the invention to provide an air purifying apparatus which will effectively kill bacteria, viruses, and the like, as well as filter out contaminants, and harmful or hazardous gasses from a ventilation system, or in an enclosed space.

SUMMARY OF THE INVENTION

The foregoing disadvantages of prior devices can be overcome by the present invention by providing a ventilation system, which comprises a housing enclosing a purifying chamber, the housing having an inlet for drawing in contaminated air and an outlet for expelling purified air; a pump for introducing a fluid containing a source of antimicrobial ions into the purifying chamber; at least one microwave radiation source and at least one ultraviolet radiation source, the radiation sources for increasing the effectiveness of antimicrobial ions in destroying airborne microorganisms; a filter for removing airborne particulates; and a filter for adsorbing antimicrobial ions from treated air. Preferably, the antimicrobial ions are derived from a halogen, such as chloride, bromide, or iodide, or a gas or fluid containing chlorine or bromine ions in another form such as hypochlorite ions, for example. The fluid can also be sprayed droplets or vaporized aqueous sodium hypochlorite or similar, antiseptic agent. The apparatus or module can be installed in a new or existing ventilation system, or can be a free standing module.

The module can include a filtration system to remove and collect airborne particles, using physical or electrostatic separation methods, and can also include a filter to adsorb harmful gasses, toxins, or poisons.

The invention also provides a method for cleaning air in a ventilation system, the method comprising: moving a volume of air into a purifying chamber; introducing an ionized antimicrobial fluid in the presence of ultraviolet and microwave energy; and maintaining the volume of air in the purifying chamber for a period of time sufficient to kill airborne microbial matter therein.

BRIEF DESCRIPTION OF THE DRAWINGS

Other objects, features and advantages of the invention may be understood by reviewing the following detailed description of the preferred embodiments in conjunction with the attached drawings in which.

DETAILED DESCRIPTION OF THE PREFERRED EMBODIMENTS

Figure 1:
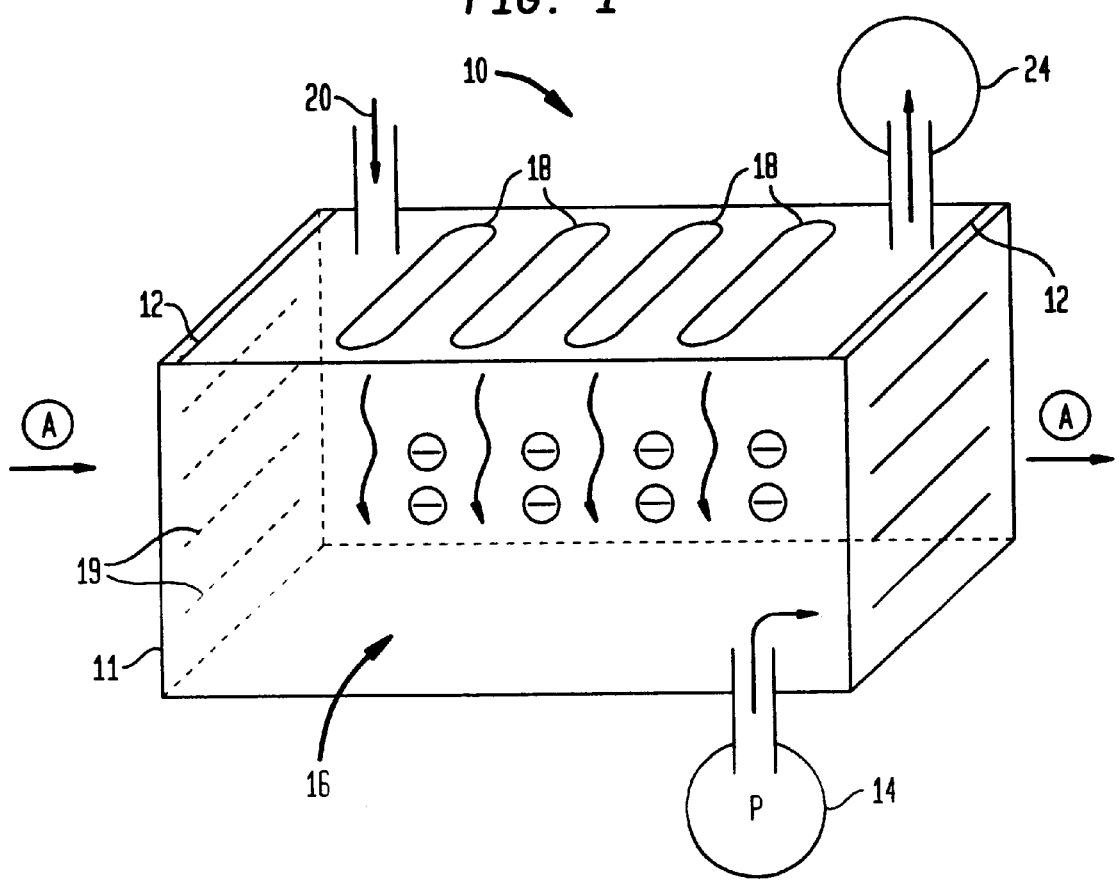
FIG. 1 is a schematic drawing of a first embodiment the air purifier of the present invention.

Referring now to the drawings, a first embodiment of the present invention is shown in FIG. 1. The air purifier 10 includes an air inlet 11 to allow air to enter the system through slits or vents 19. The air passes through a fine grid filter 12, and into the purifying chamber 16 of the purifier 10. Intake may be controlled by an external pumping apparatus forming a part of a conventional forced air heating, air conditioning or ventilation system (not shown), or can include a pump 14 which draws air into the chamber 16 or through the chamber.

Alternatively, there can be a separate pump for intake and outflow, or two or more pumps to control and direct the flow of air into and out of the purifying chamber 16. A person of ordinary skill can select, adapt, and position the pumps to fit the ventilation needs of the building, room or other enclosed space.

In any case, the air purifier 10 can be installed in the duct work or other part of a heating, ventilating, and air conditioning system. The pump 14, even in such an environment, can boost the efficiency or turnover rate of air passing through the purifier 10.

The air purifier 10 of the present invention uses a plurality of ultraviolet and microwave radiation sources 18 to irradiate the purifying chamber 16 through which contaminated air or other fluid passes through. Optionally, the air purifier 10 may include a plurality of vents 19, which may be open or closed using conventional mechanical or electrically controlled louvers to start, stop, or regulate air flow into and out of the purifying chamber 16. The air purifier 10 also includes a pump 24 with an electrostatic or other means of removing particulates from purified air.

Additionally, the air purifier 10 includes an inlet 20 or series of spigots (not shown) which introduce a fluid, such as a halogen gas (e.g., chlorine, iodine or bromine), ozone, a peroxide containing gas, chlorine dioxide gas, or a chlorine or chlorine and oxygen containing compound, such as calcium, potassium, or sodium chloride or calcium or sodium hypochlorite. Other sources of chloride, iodide, or bromide ions or chlorine and oxygen containing ions may also be used. Fluid containing chlorine atoms, such as aqueous sodium hypochlorite (common household bleach) can be vaporized or sprayed into the chamber 16 as a mist of droplets. In such a case, the fluid will include chlorine and oxygen containing atoms, molecules or ions which will kill bacteria, viruses, or other microbial contaminants in the air. It can be fortified by adding ozone to the air inside the chamber, or by adding a separate ozone treatment zone (not shown) to the system. The purifying chamber 16 should preferably be sealed from the ambient environment to avoid seepage or discharge of harmful gasses using gaskets, seals and the like.

Ultraviolet and microwave radiation ionizes or energizes the cleansing gas or fluid so that it can react with and destroy airborne biological or microbial material. The microwave and ultraviolet radiation by itself would not necessarily kill bacteria or other contaminants, but would help, for example, the chlorine, ozone, peroxide or other gas to work more effectively.

The contaminated air A is maintained for a time in the purifying chamber 16 sufficient to allow the energized ions, atoms, or molecules to kill the microbes including bacteria and viruses contained in the air. U.S. Pat. Nos. 3,817,703 (Atwood) and 5,364,645 (Lagunas-Solar) both address using various forms of electromagnetic radiation to kill pathogens and microorganisms, and set forth suggested time and energy levels which may be effective in the present apparatus and method. The contents of those patents are incorporated by reference herein.

Figure 3:
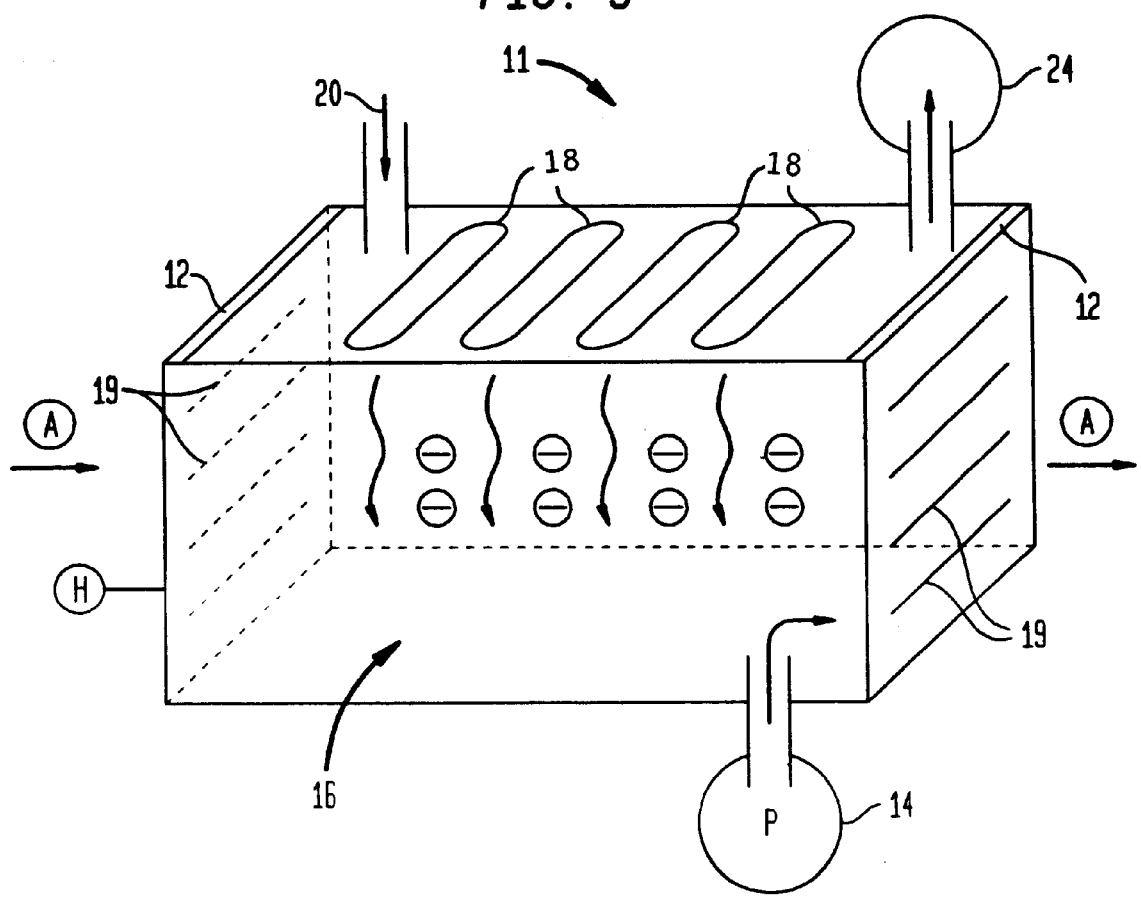
FIG. 3 is a schematic drawing of a second embodiment of the present invention.

In a second embodiment, shown schematically in FIG. 3, the air purifier 10 can be in the form of a self-contained module 11 for use in cleaning the air in a smaller facility such as a room, a home, an office, or an apartment. Like the previous embodiment, module 11 could include one or more means for introducing an antimicrobial fluid into a purifying chamber 16 defined by the housing H. The module 11 also includes one or more ultraviolet and microwave radiation sources 18 which may be separate or included in a single unit, as with the previous embodiment. The second embodiment, like the first, includes a pump 24 for removing antimicrobial fluid from the purifying chamber 16. The chamber 16, in any embodiment, should preferably include a series of vents 19 for intake and expulsion of air. It should also include baffles and gaskets to prevent the antimicrobial gas or other fluid, as well as the radiation, from escaping from the chamber 16.

A laser 54, such as an excimer laser (see FIG. 2) can provide also high intensity light energy to kill microbes. Examples of methods using laser and ultraviolet radiation to disinfect foods may be found in U.S. Pat. Nos. 5,364,645 (Lagunas-Solar), and 3,817,703 (Atwood), referenced above. Optionally, an x-ray or other radioactive source (not shown) can be added, to be used in combination with the high power microwave and UV energy sources incorporated into the present invention.

Figure 2:
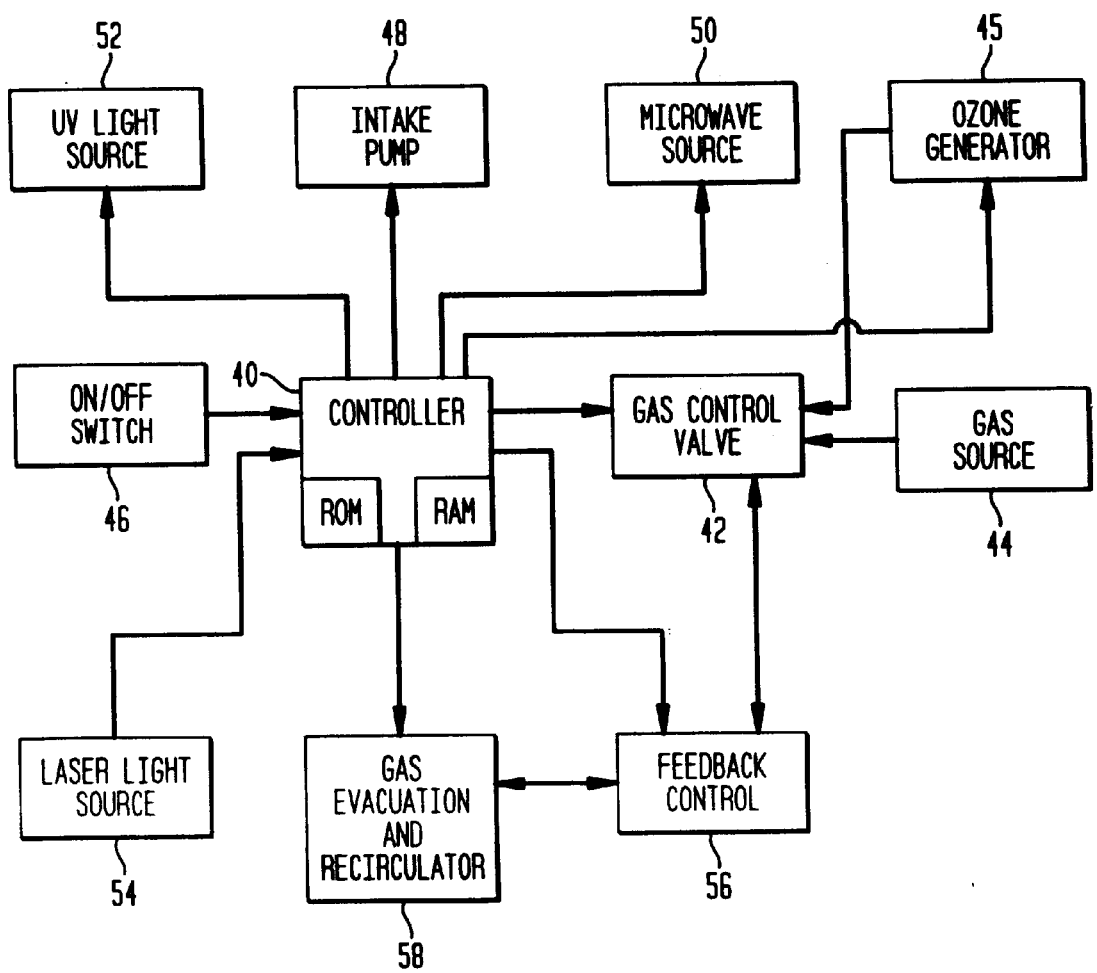
FIG. 2 is a block diagram of circuitry for controlling an air purifier according to an embodiment of the present invention.

The apparatus 10 also includes a feedback control system 56, whose operation may be understood with reference to FIG. 2. The 56 system includes a controller 40 to control the amount and type of energy and gasses released during the operation of the system. Controller 40 includes preprogrammed ROM to control the pump 48 which draws air into the chamber 18 (see also FIGS. 1 and 3, reference numeral 12).

Controller 40 also controls one or more solenoid or similar type gas or fluid valves 42 through a feedback loop so that the proper disinfecting concentration of gas or fluid (for example, ozone, peroxide, chloride, or chlorine) is fed from the gas source 44 or ozone generator 45 into the treatment chamber 16 (FIGS. 1 and 3) of the apparatus 10. The system 10 is activated by an on/off switch 46 which activates the intake pump 48, if included. The controller 40 also switches and controls the microwave radiation source 50, the ultraviolet light source 52, and the optional laser light source 54. The controller 40 either includes, or works in tandem with a feedback control system 56 to regulate the flow of gas, and the intensity of light or energy in the treatment chamber 18. The system 10 preferably includes a gas evacuation and recirculating system 58, including a filter for particulate matter, so that gas used in the treatment apparatus 10 can be reclaimed and recycled or reused.

Controller 40 can be any suitable type of controller circuit and, for example, can be a microprocessor controller. Various types of controllers suitable for use in a device such as the present invention are known in the art. Accordingly, controller 40 will not be described in detail. Briefly, however, controller 40 includes ROM for storing one or more operating programs. Controller 40 can also include RAM that can be programmed by the user through use of an alphanumeric control pad (not shown). Of course, controller 40 can also include various other types of memories and/or peripherals or peripheral interfaces as desired. Controller 40 can also be preprogrammed or can be programmed by the user to automatically run in cycles.

The UV light source may be a monochromatic beam of pulsed ultraviolet or ultraviolet laser radiation having a wavelength of about 200 to 400 nm, preferably 240–280 nm. Any type of ultraviolet source producing enough energy to kill pathogens, including Hg lamps emitting 200 nm UV radiation, or low intensity (0.10–10 W/m$^2$) continuous wave polychromatic (broad band) UV radiation can be used. Also desirable would be low intensity (0.10 to 10 W/m$^2$) continuous wave polychromatic (broad band) UV radiation (4.88 eV). Pulsed (20 nsec) ultraviolet laser radiation of 193 nm (6.42 eV) may also be used under certain conditions.

In the operation of the preferred embodiment, with reference to FIGS. 1, 2 and 3, the pump 48 activates when the on/off switch 46 is turned "on". The high intensity UV light sources 52 and microwave radiation sources 50 irradiate the air A or other fluid passing through the purifying chamber. The controller 40 opens the solenoid or other control on the gas or fluid control valve 42, allowing gas or fluid to enter from its source or container, such as a gas tank 44, into the chamber 16. The high intensity UV and microwave radiation ionizes the fluid (for example chloride ions derived from aqueous hypochlorite solution sprayed into the chamber 16), which in turn kills microbes, such as anthrax or other harmful bacteria or viruses. The contaminated gas is removed by the pump 24 (FIG. 1), which includes a filter 14 to remove and accumulate destroyed biological material and other particulate matter using electrostatic or physical filtration methods. It may also includes a module to separate and cleanse the gas so that some or all may be reused.

Various modifications in the construction of the present apparatus 10 may be made to adapt it to a particular type of ventilation system, or to adapt it to particular environmental or atmospheric contaminants. For example, the system can include an activated charcoal or other type of filter to adsorb harmful or poisonous gasses. The appropriate adsorbent material may be selected to remove a given gaseous toxic substance. While several embodiments have been shown and described, it will be apparent to those skilled in the art that other adaptions and modifications can be made without departing from the spirit and scope of the invention.

I claim:

1. An apparatus for purifying the air in a ventilation system, comprising:

a housing enclosing a purification chamber, the housing having an inlet for drawing in contaminated air and an outlet for releasing purified air;

an inlet for introducing a fluid containing a source of antimicrobial ions into the purifying chamber;

at least one microwave radiation source and at least one ultraviolet radiation source, the radiation sources for increasing the effectiveness of antimicrobial ions in destroying airborne microorganisms;

a filter for removing airborne particulates; and a filter for adsorbing antimicrobial ions from treated air.

2. An apparatus in accordance with claim 1 additionally comprising a pump for drawing contaminated air into the purifying chamber.

3. An apparatus in accordance with claim 1 additionally comprising a pump for drawing contaminated air through the purifying chamber.

4. An apparatus in accordance with claim 1, wherein the fluid is aqueous sodium hypochlorite, potassium hypochlorite, or a fluid containing chloride, bromide or iodide ions.

5. An apparatus in accordance with claim 1 wherein the antimicrobial fluid is ozone, a peroxide, a halogen gas, or chlorine dioxide.

6. An apparatus in accordance with claim 1, additionally comprising a pump for removing contaminated air from the purifying chamber.

7. A method for destroying microbes in contaminated air flowing through a vent system, the method comprising: moving the contaminated air through a purifying chamber; introducing antimicrobial fluid in the presence of ultraviolet and microwave energy wherein the ultraviolet and microwave energy ionizes the antimicrobial fluid while the air passes therethrough; and retaining the air in the purifying chamber for a sufficient time to kill microbial matter in the air.

8. A method in accordance with claim 7, wherein the microwave and ultraviolet energy from the microwave and ultraviolet sources energize the ions in the antimicrobial fluid.

9. A method in accordance with claim 8 wherein the ions in the antimicrobial fluid is chloride, bromide or iodide.

* * * * *